Figure 3:
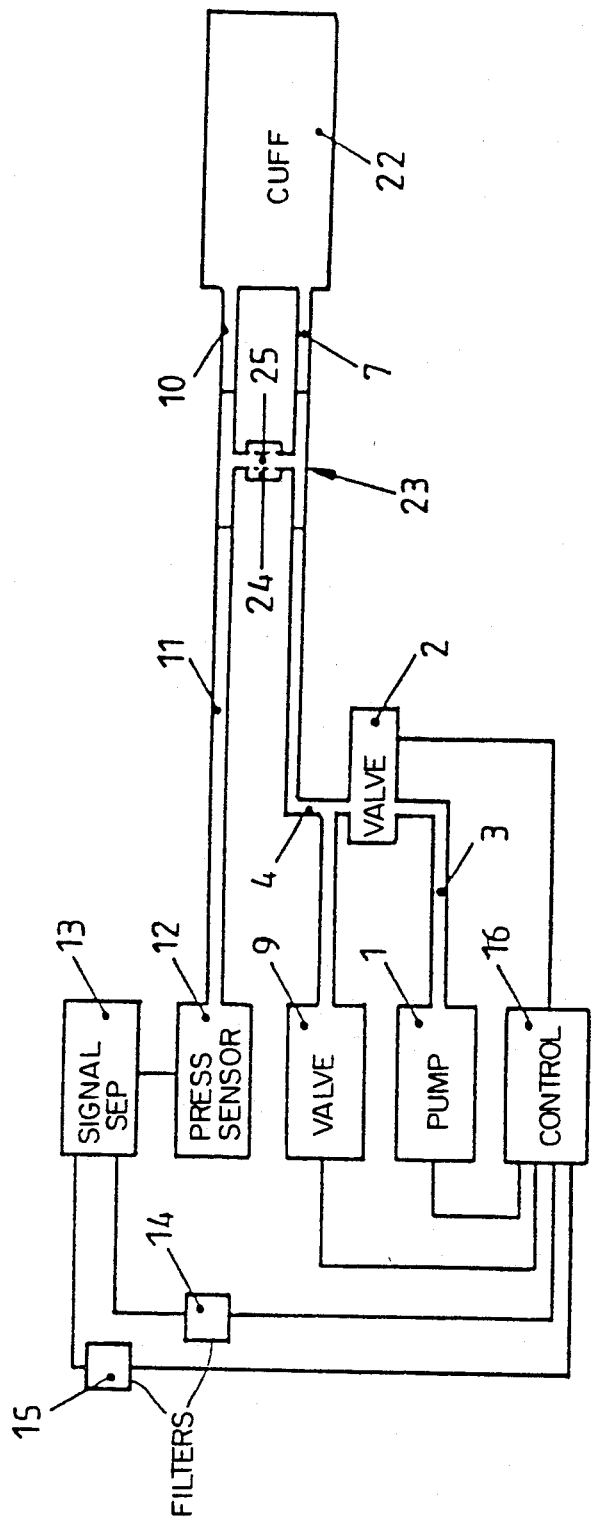

United States Patent [19]

Malkamäki et al.

[11] Patent Number: 5,060,654
[45] Date of Patent: Oct. 29, 1991

[54] IDENTIFICATION METHOD FOR THE CUFF TYPE OF A SPHYGMOMANOMETER

[75] Inventors: Lauri Malkamäki, Vantaa; Lauri P. Kankkunen, Espoo, both of Finland

[73] Assignee: Instrumentarium Corporation, Finland

[21] Appl. No.: 493,352

[22] Filed: Mar. 14, 1990

[30] Foreign Application Priority Data

Mar. 17, 1989 [FI] Finland ............................ 891289

[51] Int. Cl.$^5$ ............................................. A61B 5/02
[52] U.S. Cl. ................................... 128/686; 128/677
[58] Field of Search ..................... 128/672, 677–683, 128/685, 686; 606/202

[56] References Cited

U.S. PATENT DOCUMENTS

| | | | |
|---|---|---|---|
| 3,812,844 | 5/1974 | Sokol | 128/686 |
| 4,210,154 | 7/1980 | Klein | 128/686 |
| 4,501,280 | 3/1985 | Hood, Jr. | 128/677 |
| 5,003,981 | 4/1991 | Kankkunen et al. | |

Primary Examiner—Stephen C. Pellegrino
Assistant Examiner—Longo Robin R.
Attorney, Agent, or Firm—Andrus, Sceales, Starke & Sawall

[57] ABSTRACT

The invention relates to an automatic identification method for the cuff of a sphygmomanometer. A positive pressure is utilized for triggering a pulse from a valve (2) to a pressure sensing element (12) followed by measuring the width of a detected pulse. The measured pulse width is compared with a predetermined pulse width threshold value and, on the basis of this comparison, a larger and a smaller cuff are distinguished from each other, as the measured pulse width indicates the presently used cuff size.

14 Claims, 2 Drawing Sheets

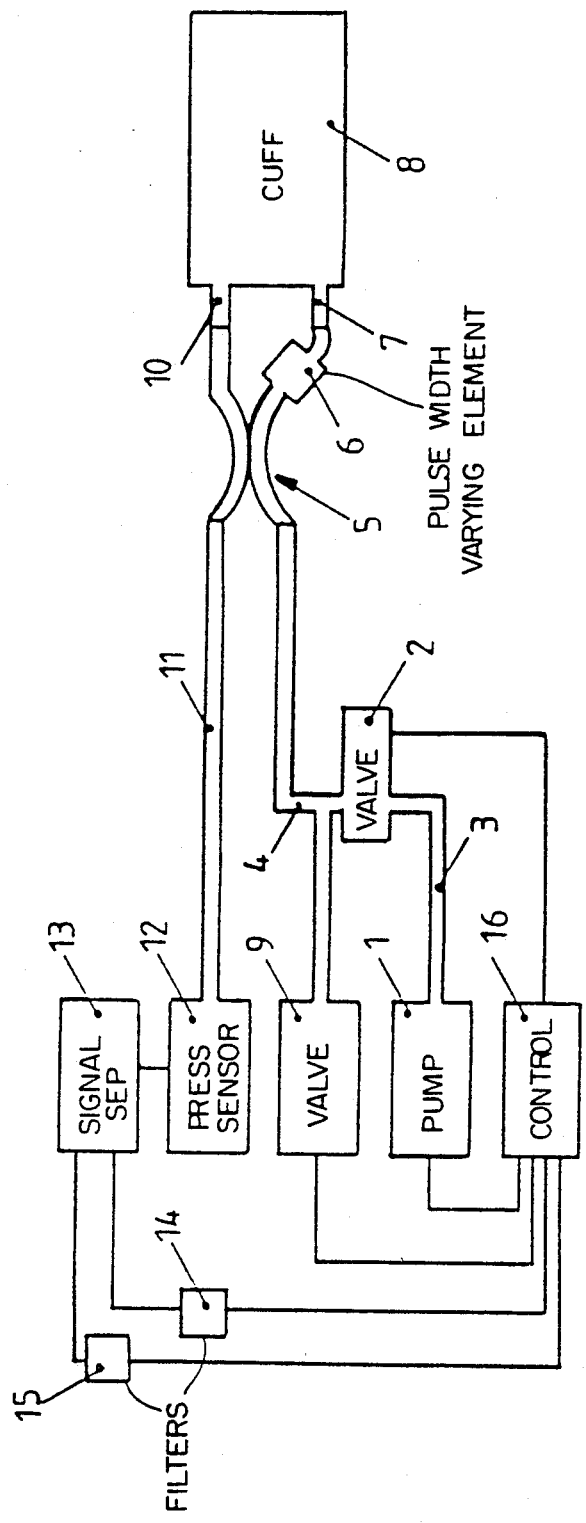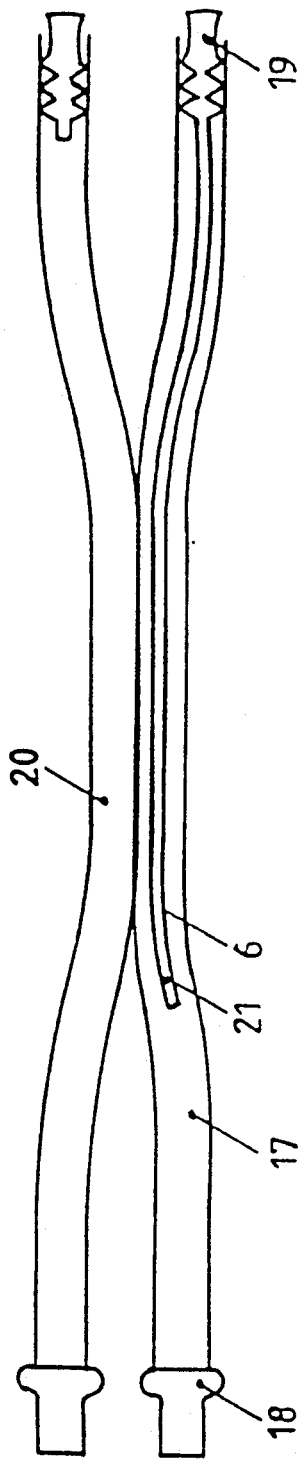

IDENTIFICATION METHOD FOR THE CUFF TYPE OF A SPHYGMOMANOMETER

The present invention relates to an identification method for the cuff type of a non-invasive automatic sphygmomanometer, said method making use of a pressure or a sound pulse.

In some devices, the selection of cuffs intended for adults and newborn babies is effected by means of a selector switch mounted on the device. Thus, the selector switch is used for manually selecting the operation mode for the device according to whether the question is about an adult or a newborn baby. However, there is always a hazard of forgetting to change the position of a selector switch e.g. when replacing a cuff intended for adults with the one intended for newborn babies. Such a lapse could cause even serious damage to newborn babies.

U.S. Pat. No. 4,501,280 discloses a method developed for the automatic identification of a cuff size. A certain pressure is pumped in the cuff followed by opening a valve for lowering pressure in the cuff. Opening of the valve produces a sound pulse which travels along a tubing to the cuff and further to a detector which calculates the time from the opening of valve to the arrival of sound pulse at the detector The arrival time of a sound pulse at the detector varies according to the size of a cuff. This delay time of a sound pulse can be further adjusted by shortening the tubing leading to the cuff intended for newborn babies as compared to the length of a tubing leading to the cuff intended for adults The delay time of a sound pulse can be further cut down by fitting the tubing leading to a cuff intended to newborn babies with a side tubing directly to a tubing leading from cuff to detector. On the basis of the delay time, a microprocessor ascertains whether the question is about a cuff for adults or newborn babies One problem in the solution set forth in the cited U.S. Patent application based on a sound pulse is that it is not possible to employ tubings of arbitrary length leading from the pressure transmission system to the cuff, since the program according to this system involves measurement of a pulse passage time which, in turn, is restricted by certain limits of acceptance. However, certain practical cases require tubings which should either be substantially shorter or longer than the tubings used in connection with a system of the invention. The cuffs intended for adults and children cannot be operated safely by using tubings of equal lengths, since the identification of a cuff size may become more difficult.

More problems result from the fact that, if a cuff is to be replaced with the one of a different size, the entire long tubing must also be replaced The successful use of a short adapter is not possible Also known is a method of pumping in a cuff a certain pressure followed by calculating a time lapsed from the attainment of said pressure to the dropping thereof The basis of this idea is that the outflow of air is dependent on the size of a cuff. The longer the time this outflow takes, the larger is the cuff in question A problem in this solution is the clogging of a cuff or a cuff tubing which in the worst case may lead to incorrect identification of the size of a cuff. The clogging of a tubing may markedly extend the time spent for the deflation of a cuff.

Automatic identification of a cuff size can be also be achieved by measuring the time spent for pumping a certain pressure in a cuff. Thus, the pumping time in connection with a larger cuff is longer than in the case of a smaller cuff. Problems in this type of solution include faults in the mains and variation of the pump characteristics, which may lead to serious mistakes in the identification of a cuff.

An object of this invention is to eliminate the above problems. Thus, the objective is to provide a reliable, automatic cuff identification method which is independent of the variations in pump characteristics and of the mains disturbances and which facilitates the use of tubings of arbitrary length that need not be necessarily replaced whenever a cuff is replaced with the one of a different size. Another object is to provide a cuff type identification test which can be conducted quickly at a moment free of the movement artifacts of a patient. A further object is to provide a pressure measuring system for intensifying the detectable pressure pulses applied to a cuff.

The characterizing features of a cuff type identification method of the invention are set forth in the annexed claims.

The invention relating to identification of a cuff type is based on using a pressure sensing element, which at the same time serves as a microphone, for monitoring the width of a pressure or sound pulse which is transmitted through a rapidly opening and closing valve and which is as narrow as possible. The pulse width can be affected by changing a pulse response between the valve and the pressure sensing element.

The most preferable result is obtained by increasing the pulse width detected by means of a pressure sensing element more when using a smaller cuff than when using a larger cuff. In practice, this can be preferably achieved e.g. by placing a pulse response altering means in connection with children's cuffs and, on the other hand, by omitting it completely when identifying an adults' cuff. Of course, the very opposite procedure is also possible.

Thus, a pulse transmitted through a rapidly opening and closing valve is carried either directly or by way of a pulse response varying element to a pressure sensing element. On its way to a pressure sensing element, said pulse can travel through a cuff or bypass it.

A control element responsible for the automatic identification is assigned a given pulse width value, e.g. a value within the range of pulse width values obtained in connection with the use of a larger and smaller cuff, the pulse width values obtained in a measuring procedure being then compared to that value. When the pulse width exceeds this threshold value, the control element identifies the presently used cuff as a smaller, and respectively, as a larger cuff provided that the pulse width is narrower than the threshold value. Thus, in this case, a pulse response varying element, which causes the widening of a pulse detected by means of a pressure sensing element, has been used in connection with a smaller cuff.

Figure 4B:
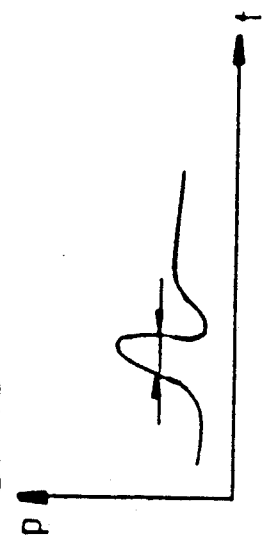
Figure 4A:
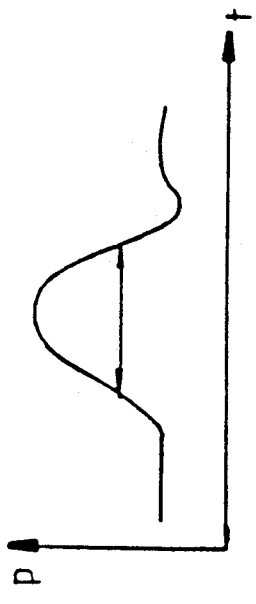

The invention will now be described in more detail with reference made to the accompanying drawings, in FIG. 1 shows a schematic view of an apparatus, used in a cuff type identification method of the invention and provided with a cuff intended for newborn babies, FIG. 2 shows a cross-sectional view of one preferred, separate
spacer block, used in the cuff type identification apparatus of FIG. 1 and attached to a tube leading to a cuff, FIG. 3 shows a schematic view of an apparatus, used in a cuff type identification method of the invention and provided with a cuff intended for adults, FIGS. 4a and 4b illustrate the principle for an identification method of the invention for distinguishing two different cuff types from each other.

FIG. 1 illustrates a schematic view of an apparatus used in a cuff type identification method. The case shown in this FIGURE relates to measuring the blood pressure of a newborn baby. A tubing 3 leads from a pump 1 to a rapid-action on-off valve 2. Suitable on-off valves include e.g. a solenoid valve, a piezoelectric valve and a magnetostrictive valve. From valve 2 leads another tubing 4 to a spacer block 5 which is provided with a pulse response varying element 6. From the spacer block there is a connection through the intermediary of a tubing 7 to a cuff 8. An outlet valve 9 is also preferably in communication with the tubing leading from on-off valve 2 to spacer block 5. On the other hand, there is a tubing 10 running from the cuff to spacer block 5 and from there another tubing 11 to a pressure sensing element 12. A signal obtained from the pressure sensing element passes by way of an AC/DC signal separator 13 and filters 14 and 15 to a control element 16 which is capable of identifying a cuff type on the basis of a received signal The operation of valves 2 and 9 as well as pump 1 is also controlled by said control element 16, preferably a microprocessor.

The spacer block 5 is shown in more detail in a longitudinally cross-sectional view of FIG. 2. Thus, a tubing 17 from spacer block 5 is attached to a conventional tubing 4 leading from valve 2 to cuff 8 by means of a clamp member 18 or 19. To the other end of tubing 17 of spacer block 5 is attached a cuff by means of the available clamp member 19 or 18 through the intermediary of tubing 7. The spacer block 5 is also provided with a tubing 20 to be fitted between tubings 10 and 11 extending from cuff 8 to pressure sensing element 12. Inside the spacer block tubing 17 is a pulse response varying element 6, provided with an aperture 21 for passing a pressure or sound pulse therethrough. This element is preferably tubular in structure. The pulse response varying element can have a diameter which is the larger the longer said element 6 is and of course vice versa. Thus, the element 6 must widen a pulse sufficiently in order to make the control element 16 capable of sufficiently distinguishing a larger and a smaller cuff from each other on the basis of measurement values received from pressure sensing element 12.

FIG. 3 illustrates a schematic view of an apparatus used in a cuff size identification method for measuring the blood pressure in adults. The only difference from FIG. 1 is that a spacer block 5 is replaced with a connecting piece 23 joining the tubings coming to a cuff 22. In such connecting piece, a pulse response varying element 24 comprises simply a connecting tube 25 for connecting a tubing 4 leading from on-off valve 2 to cuff 22 and a tubing 11 leading from cuff to pressure sensing element 12. The purpose of connecting tube 25 is to narrow a pulse detected by pressure sensing element 12. In this case, said pulse response varying element 24 operates in a reverse mode compared to what is shown in FIG. 1.

FIGS. 4a and 4b illustrate the AC components separated by means of an AC/DC signal separator 13 from the signals received from pressure sensing element 12, said AC components being shown as a function of pressure (P) and time (t). The AC component is a high-speed and high-frequency signal. On the other hand, the filteredout DC component is a slow signal. FIG. 4a illustrates a signal obtained by an apparatus of FIG. 1 and FIG. 4b illustrates a signal obtained by an apparatus of FIG. 3.

Prior to the identification of a cuff, a pumping action is commenced by means of a pump 1 for producing a positive pressure followed by opening an on-off valve 2 for a short period, e.g. for 10 ms. A pressure or sound pulse travels either through cuff 8 or 22 or bypasses it to pressure sensing element 12, which also serves as a microphone. On the basis of a signal transmitted from the pressure sensing element, a control element calculates the pulse width. The control element 16 has been supplied with a certain threshold value for the pulse width or pulse duration, the control element effecting a comparison with such value for identifying a larger and a smaller cuff from each other as the measured pulse width settles on either side of said threshold value. If the pulse width exceeds a threshold value set on the control element, as in FIG. 4a, the control element identifies it as a small cuff since it is specifically a small cuff which in this case is provided with a pulse response varying element 6 for decelerating the propagation of a pulse. On the basis of the obtained information, such control element adapts the operations of an apparatus to what is required by a small cuff 8. It is preferable that the cuff size be also considered when discharging pressure out of a cuff.

If a pressure pulse produced by an on-off valve has a duration of 10 ms, the pressure pulse width detected by means of a pressure sensing element is appr. 170 ms when a pulse response varying element 6, which thus widens the detected pulse, is in position This result is of course highly dependent e.g. on the properties of a presently used pulse response varying element 6.

On the other hand, if the pulse width goes below a threshold value, as in FIG. 4b, the control element identifies it as a large cuff as there are no such pulse response varying elements 6 that would widen the pulse. When a pressure pulse issued by an on-off valve has a duration of 10 ms, the pulse width detected by means of a pressure sensing element has a duration of appr. 35 ms. Also this value depends on a variety of factors.

A single pressure pulse is sufficient, but in order to be absolutely certain about a presently used cuff type, a preferred practice is to run two or three tests to determine the cuff type. Identification is preferably conducted as soon as the inflation of a cuff begins. However, the identification can still be done during the course of cuff inflation by shutting down the flow for a short moment by closing an on-off valve 2 and by re-opening it for a short moment. The identification of a cuff type is preferably done every time prior to the next measurement of blood pressure unless the measurements take place immediately after one another.

In order not to accidentally connect a larger cuff to a spacer block 5, it is preferable to provide spacer block 5 with such an attachment which is only compatible with small cuffs. It is also preferred that a smaller cuff could not be directly attached to tubings 4 and 11 without a spacer block 5 fitted with a pulse response varying element 6, the latter thus serving to widen a pulse. The connecting piece 23 should also be provided with an attachment which prevents the connection thereof with a smaller cuff.

The invention is by no means limited to the above embodiments but various details of the invention can of course be modified within the scope of the claims. The identification of a cuff type can be performed in a reversed order to what is described above, i.e. by varying a pulse response prevailing between valve 2 and pressure sensing element 12 in a manner that the pulse width increases when the question is about the identification of a larger cuff In this case, the identification of a smaller cuff would not require a pulse response varying element at all or, if such element is used, it should in fact narrow a pulse detected by means of a pressure sensing element.

A pulse response varying element 6, fitted in a spacer block for widening a detected pulse, can of course be substantially different from the embodiment shown in FIG. 2. A single tube or tubing can be replaced with a plurality of tubes or tubings either in parallel or successive relationship. Another solution is e.g. a perforated plate, which is thus provided with one or more apertures, to serve as a pulse response varying element. The pulse response varying element 6 can possibly consist merely of obstacles, such as strips, placed in aperture 21 or in tubes 4, 5 or 7. These are a few example of possible embodiments but other solutions exist as well. The significant feature is after all the capability of varying a pulse response between a valve and a pressure sensing element.

A separate spacer block 5 is not absolutely necessary either, since a pulse response varying element 6 can also be placed in a tubing 7 leading to cuff 8 or even in cuff 8 itself or also in tubing 4. A pulse response varying tube or tubing need not necessarily be placed inside any tubing, e.g. a spacer block, but it can be a part of a tubing leading from a pump or a valve to a cuff. The separate pulse response varying elements are not absolutely necessary but the required difference in the pulse width detected by a pressure sensing element is produced by using tubings, whose inner diameters vary according to a cuff type.

In the case of an adults' cuff, a connecting piece 23 used in FIG. 3 for joining the tubings, and a pulse response varying element 24 included therein, is not necessary as the identification of a cuff type is possible without it. Thus, a pulse triggered from valve 2 travels through cuff 22 to pressure sensing element 12. However, a connecting piece 23 is prefered for further narrowing a pulse detected by means of pressure sensing element 12.

The above discussion, in reference to the drawings, has primarily dealt with the identification of an adults' cuff and a cuff intended for children and particularly for newborn babies. Naturally, the possible identification is not restricted to just these two different types of cuffs but the present identification system is useful also for the identification of cuffs of other sizes. If necessary, this system can be applied to the identification of more than two different types of cuffs by employing pulse response varying elements which are capable of producing sufficient differences in the pulse width detected by means of a pressure sensing element.

FIGS. 1 and 3 show that there is a single common tubing 4 leading to a cuff from on-off valve 2 and from outlet valve 9. Valve 9 and pump 1 can of course have each their own tubing extending directly to a cuff. In this case, a pulse response varying element 6 must be placed at least in a tubing between a pump and a cuff when the question is about a smaller cuff, but possibly also in a tubing leading from a valve to a cuff.

We claim:

1. A method for identifying the properties of a cuff connected in a sphygmomanometer by a fluid communication system having a pressurizing means and a sensor, said method comprising the steps of:
    generating a pressure pulse in the fluid communication system, said pulse having a predetermined pulse width;
    transmitting the pulse int he fluid communication system;
    altering the width of the pulse during its transmission when a cuff having certain properties is connected in the sphygmomanometer;
    sensing the width of the pulse subsequent to transmission in the fluid communication system;
    comparing the width of the sensed pulse with a predetermined value; and
    determining, on the basis of said comparison, the properties of the cuff connected in the sphygmomanometer.

2. A method as set forth in claim 1 further defined a generating a pressure pulse having acoustical characteristics.

3. A method as set forth in claim 2 further defined as sensing the width of the pulse by means of a sensor responsive to the acoustical characteristics of the pulse.

4. A method as set forth in claim 1 further defined as transmitting the pulse along a path in the fluid communication system that includes the cuff.

5. A method as set forth in claim 1 further defined as transmitting the pulse along a path in the fluid communication system that bypasses the cuff.

6. A method as set forth in claim 1 further defined as generating the pulse by means of a high-speed on-off valve coupled to said pressurizing means.

7. A method as set forth in claim 6 further defined as generating the pulse by means of a valve which is one of a solenoid valve, piezoelectric valve and a magnetostrictive valve.

8. A method as set forth in claim 1 further defined as one for determining the size of the cuff connected in the sphygmomanometer.

9. A method as set forth in claim 8 further defined as one for determining which of a larger or smaller size cuff is connected in the sphygmomanometer, and as altering the width of the pulse, during its transmission, to a magnitude greater than the predetermined value when the smaller size cuff is connected in the sphygmomanometer.

10. A method as set forth in claim 8 further defined as one for determining which of a larger or smaller size cuff is connected in the sphygmomanometer, and as transmitting the pulse along a path in the fluid communication system that includes the cuff when the smaller size cuff is connected in the sphygmomanometer.

11. A method as set forth in claim 8 further defined as one for determining which of a larger or smaller size cuff is connected in the sphygmomanometer, and as transmitting the pulse along a path in the fluid communication system that bypasses the cuff when the larger size cuff is connected in the sphygmomanometer.

12. A method as set forth in claim 8 further defined as one for determining which of a larger or smaller size cuff is connected in the sphygmomanometer, and as transmitting the pulse along a path in the fluid communication system that includes the cuff when the larger size cuff is connected in the sphygmomanometer.

13. A method as set forth in claim 1 further defined as one for determining the size of the cuff connected in the sphygmomanometer.

14. A method for identifying which of a larger or smaller size cuff is connected in a sphygmomanometer by a fluid communication system having a pressurizing means and a sensor, said method comprising the steps of:

generating an acoustical pulse in the fluid communication system, said pulse having a predetermined pulse width;

transmitting the pulse in the fluid communication system;

increasing the width of the pulse, during its transmission, when a smaller size cuff is connected in the sphygmomanometer;

sensing the width of the pulse subsequent to transmission in the fluid communication system;

comparing the width of the sensed pulse with a predetermined valve having a magnitude less than the increased width of the pulse; and determining, on the basis of said comparison, that the smaller size cuff is connected in the sphygmomanometer when the pulse width magnitude of the sensed pulse exceeds the predetermined value.

* * * * *

UNITED STATES PATENT AND TRADEMARK OFFICE
CERTIFICATE OF CORRECTION

PATENT NO. : 5,060,654
DATED : October 29, 1991
INVENTOR(S) : Lauri Malkamäki, et al It is certified that error appears in the above-identified patent and that said Letters Patent is hereby corrected as shown below:

Column 6, line 11    delete "int he" and substitute therefor ---in the---

Column 6, line 23    delete "a" and substitute therefor ---as---

Column 7, lines 3-5  delete claim 13 in its entirety and substitute therefor:

--- 13. A method as set forth in claim 1 further defined as altering the width of the pulse, during its transmission, to a magnitude greater than the predetermined value when a cuff of predetermined properties is connected in the sphygmomanometer. ---

Signed and Sealed this

Fifteenth Day of June, 1993

Attest:

MICHAEL K. KIRK

*Attesting Officer*    Acting Commissioner of Patents and Trademarks